United States Patent
Dernbach et al.

(10) Patent No.: US 6,586,642 B2
(45) Date of Patent: Jul. 1, 2003

(54) COLOR NUMBER IMPROVEMENT IN POLYHYDRIC ALCOHOLS BY HYDROGENATION

(75) Inventors: Matthias Dernbach, Dossenheim (DE); Detlef Kratz, Heidelberg (DE); Achim Stammer, Freinsheim (DE); Mathias Haake, Mannheim (DE); Michael Koch, Speyer (DE); Gerhard Schulz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/168,986
(22) PCT Filed: Dec. 28, 2000
(86) PCT No.: PCT/EP00/13328
§ 371 (c)(1), (2), (4) Date: Jun. 26, 2002
(87) PCT Pub. No.: WO01/47850
PCT Pub. Date: Jul. 5, 2001

(65) Prior Publication Data
US 2003/0045760 A1 Mar. 6, 2003

(30) Foreign Application Priority Data
Dec. 28, 1999 (DE) .......................... 199 63 442

(51) Int. Cl.$^7$ .......... C07C 27/26; C07C 29/74; C07C 31/18; C07C 27/00; C07C 27/04
(52) U.S. Cl. .......... 568/854; 568/863; 568/868; 568/869
(58) Field of Search .......... 568/854, 853, 568/852, 861, 862, 863, 868, 869, 864, 870

(56) References Cited

U.S. PATENT DOCUMENTS

| | | |
|---|---|---|
| 3,097,245 A | 7/1963 | Russell |
| 5,603,835 A | 2/1997 | Cheung |

FOREIGN PATENT DOCUMENTS

| | | |
|---|---|---|
| DE | 1 768 259 | 10/1971 |
| EP | 601 571 | 6/1994 |
| GB | 1168216 | 10/1969 |

Primary Examiner—Johann Richter
Assistant Examiner—Elvis O. Price
(74) Attorney, Agent, or Firm—Keil & Weinkauf

(57) ABSTRACT

A process for greatly improving the color index of polyhydric alcohols, especially trimethylolpropane, by hydrogenation comprises using, in the hydrogenation, an alcohol which has already been purified by distillation. The catalysts used are those conventionally employed in hydrogenations, preferably copper, nickel, palladium or ruthenium catalysts.

18 Claims, No Drawings

COLOR NUMBER IMPROVEMENT IN POLYHYDRIC ALCOHOLS BY HYDROGENATION

This application is a 371 of PCT/EP00/13328, filed Dec. 28, 2000.

The present invention relates to a process which affords polyhydric alcohols of low color index by hydrogenation.

Polyhydric alcohols are obtained on a large scale by condensing formaldehyde with higher CH-acidic aldehydes or with water and acrolein or 2-alkylacroleins. This reaction can be carried out according to two main procedural variants.

Firstly, there is the so-called Cannizzaro process, which is further subdivided into the inorganic and organic Cannizzaro processes. In the inorganic variant, excess formaldehyde is reacted with the appropriate alkanal in the presence of stoichiometric amounts of an inorganic base such as NaOH or Ca(OH)$_2$. In the second step, the dimethylolbutanal formed in the first step reacts with the excess formaldehyde in a disproportionation reaction to give trimethylolpropane and the formate of the base used, i.e. sodium or calcium formate. The production of these salts is a disadvantage because they are not easy to separate from the reaction product; in addition, one equivalent of formaldehyde is lost.

In the organic Cannizzaro process, a tertiary alkylamine is used in place of an inorganic base, affording higher yields than with an inorganic base. Trialkylammonium formate is obtained as an unwanted by-product, so here again one equivalent of formaldehyde is lost.

The disadvantages of the Cannizzaro process are avoided in the so-called hydrogenation process, where formaldehyde is reacted with the appropriate aldehyde in the presence of catalytic amounts of an amine, the result being that the reaction stops at the alkylolated aldehyde stage. After separation of the formaldehyde, the reaction mixture—which, in addition to said alkylolated aldehyde, also contains small amounts of the corresponding polyhydric alcohol and acetals of the alcohols formed—is hydrogenated to give the desired polyhydric alcohol.

One particularly efficient process for the preparation of alcohols obtainable by condensing aldehydes with formaldehyde is described in WO 98/28253. This process affords high yields with the concomitant production of small amounts of coupling products. The procedure involves reacting the higher aldehyde with 2 to 8 times the amount of formaldehyde in the presence of a tertiary amine and separating the resulting reaction mixture into two solutions, one containing said fully methylolated alkanal and the other containing unreacted starting material. The latter solution is recycled into the reaction. The separation is effected by distillation or by simply separating the aqueous phase from the organic phase. The solution containing the product is subjected to a catalytic and/or thermal treatment to convert incompletely alkylolated alkanals to the desired fully methylolated compounds. By-product formed in this process is separated off by distillation and the resulting bottom product is subjected to catalytic hydrogenation to give the polyhydric alcohols.

examples of important alcohols prepared by the processes described are neopentyl glycol, pentaerythritol, trimethylolethane, trimethylolbutane and, in particular, trimethylolpropane (TMP).

TMP has become widely used as a crosslinking agent for polyesters and polyurethanes. However, commercially available grades of TMP have a more or less pronounced coloration, probably caused by the presence of impurities. This coloration is not a problem for many uses, but there are also applications for which it is desirable to use TMP with as little color as possible. A variety of processes aimed at improving the color index of TMP are described in the literature.

U.S. Pat. No. 3,097,245 describes a process for the preparation of trimethylolpropane with an APHA color index of between 50 and 200. This color index is achieved by observing specific reaction conditions in respect of temperature, reaction time, pH and concentration of the starting compounds. The reaction is also followed by treatment of the resulting solution with an ion exchange resin.

U.S. Pat. No. 5,603,835 discloses a process for the preparation of TMP with APHA color indices of <100. These are achieved by means of an extractive aftertreatment of the resulting crude TMP solutions with an ether or an ester. The TMP solutions used generally originate from the Cannizzaro process.

Both the processes described above have the disadvantage of being relatively expensive because specific conditions have to be observed precisely and it is necessary to add an ion exchange resin or introduce at least one solvent.

The literature only contains a small amount of information on the hydrogenation of products formed by condensing formaldehyde with higher aldehydes.

DE-A-17 68 259 discloses a process for the processing of the by-products formed when reacting formaldehyde with higher aldehydes to give polyhydric alcohols. The process consists in separating these by-products from the main product and then hydrogenating them to give comparatively large amounts of mainly aliphatic alcohols.

The hydrogenation process described in SU-A 125 552 is used to purify TMP obtained by the Cannizzaro process, said TMP being either a crude material in the form of an aqueous solution containing approx. 30% of TMP, or a purified material containing approx. 80% of TMP, from which water and formates have been removed. Hydrogenation on nickel, zinc, molybdenum and copper catalysts affords pure TMP with a content of approx. 98% after distillation. The pressures used are 1 to 250 bar, preferably 10 to 200 bar, and the temperatures are 20 to 200° C., preferably 100 to 150° C. The TMP obtained is said to be colorless, although no color index is mentioned.

It has been found, however, that the improvements in color index obtainable by this process are often inadequate for many purposes.

It is therefore an object of the present invention to provide a process which makes it possible to obtain polyhydric alcohols, especially TMP, with a low color index. APHA color indices of <20 should be achievable by this process.

We have found that this object is achieved by a process for improving the color index of polyhydric alcohols by catalytic hydrogenation, wherein the polyhydric alcohol used in the hydrogenation has been purified by distillation following its preparation.

The process according to the invention can be used to improve the color index of polyhydric alcohols, especially TMP, of any origin. Batches originating from the organic or inorganic Cannizzaro process can be used in the hydrogenation according to the present invention for improving the color index in just the same way as can alcohols originating from the hydrogenation process. It is important here, however, that the alcohol has been purified beforehand and is of a purity which is within an appropriate range and allows the color index to be improved by means of the process according to the invention. Particularly good results have been achieved in cases where the polyhydric alcohol used has originated from the hydrogenation process. The use of polyhydric alcohols, especially TMP, of this origin is usually preferred according to the invention.

It has been established that the use of already distilled polyhydric alcohol makes it possible to achieve an improvement in color index which is far greater than that achieved using an alcohol which has not been purified beforehand by distillation. Good results have been obtained with solutions containing >95% of alcohol.

If TMP is used in the hydrogenation, particularly good results can be achieved by using TMP solutions with a content of >98%.

The hydrogenation according to the invention is particularly applicable to any polyhydric alcohols which can be prepared by condensing formaldehyde with higher aldehydes, in the presence of catalytic amounts of trialkylamine, and then hydrogenating the products. Practically any alkanals with an acidic hydrogen atom in the α-position to the carbonyl group are suitable higher aldehydes. Starting materials which can be used are aliphatic aldehydes having from 2 to 24 C atoms which can be linear or branched or can also contain alicyclic groups. Other suitable starting materials are araliphatic aldehydes, provided that they contain a methylene group in the α-position to the carbonyl group. In general, aralkylaldehydes having from 8 to 24 C atoms, preferably from 8 to 12 C atoms, for example phenyl-acetaldehyde, are used as starting materials. Aliphatic aldehydes having from 2 to 12 C atoms are preferred, examples being 3-ethyl-, 3-n-propyl-, 3-isopropyl-, 3-n-butyl-, 3-isobutyl-, 3-sec-butyl- and 3-tert-butyl-butanal and the corresponding n-pentanals, n-hexanals and n-heptanals; 4-ethyl-, 4-n-propyl-, 4-isopropyl-, 4-n-butyl-, 4-isobutyl-, 4-sec-butyl- and 4-tert-butyl-pentanals, -n-hexanals and -n-heptanals; 5-ethyl-, 5-n-propyl-, 5-isopropyl-, 5-n-butyl-, 5-isobutyl-, 5-sec-butyl- and 5-tert-butyl-n-hexanals and -n-heptanals; 3-methylhexanal and 3-methylheptanal; 4-methylpentanal, 4-methylheptanal, 5-methylhexanal and 5-methylheptanal; 3,3,5-trimethyl-n-pentyl-, 3,3-diethylpentyl-, 4,4-diethylpentyl-, 3,3-dimethyl-n-butyl-, 3,3-dimethyl-n-pentyl-, 5,5-dimethylheptyl-, 3,3-dimethylheptyl-, 3,3,4-trimethylpentyl-, 3,4-dimethylheptyl-, 3,5-dimethylheptyl-, 4,4-dimethylheptyl-, 3,3-diethylhexyl-, 4,4-dimethylhexyl-, 4,5-dimethylhexyl-, 3,4-dimethylhexyl-, 3,5-dimethylhexyl-, 3,3-dimethylhexyl-, 3,4-diethylhexyl-, 3-methyl-4-ethylpentyl-, 3-methyl-4-ethylhexyl-, 3,3,4-trimethylpentyl-, 3,4,4-trimethylpentyl-, 3,3,4-trimethylhexyl-, 3,4,4-trimethylhexyl- and 3,3,4,4-tetramethylpentylaldehyde; $C_2$ to $C_{12}$ n-alkanals are particularly preferred.

Particularly preferred polyhydric alcohols within the framework of the present invention are trimethylolethane, trimethylolpropane, trimethylolbutane, neopentyl glycol and pentaerythritol, trimethylolpropane being very particularly preferred.

If the color index of TMP is to be improved by the process according to the invention, a TMP of high purity (>98%) prepared by the hydrogenation process can be obtained for example by the process described in the German patent application entitled "Process for the purification, by continuous distillation, of trimethylolpropane prepared by hydrogenation", reference no. 199 63 435.1 (Applicant: BASF AG). In this process, the crude product obtained after hydrogenation is first subjected to dehydration, in which water and other low-boiling components, such as methanol, trialkylamine or trialkylammonium formate, are separated off by distillation. This distillation can be carried out at pressures of <400 mbar, preferably 20 to 200 mbar, at bottom temperatures of <200° C. and for short residence times so that the trialkylammonium formate produced reacts to only a small extent with TMP to give TMP formates and trialkylamine. It is also possible to carry out the distillation at pressures of >200 mbar, preferably >400 mbar, at bottom temperatures of >140° C. and for long residence times so that at least the bulk of the TMP reacts with trialkylammonium formate to give TMP formates and trialkylamine.

The high-boiling components are then separated off in the next step. This is carried out by distilling from the bottom product, at 210 to 250° C., those components which are volatile at these temperatures. The high-boiling components thus remain in the bottom product. The low-boiling TMP-rich fraction obtained is then worked up by distillation (first distillative purification) to separate off unwanted low-boiling components. The pure product obtained can be subjected to a second distillative purification to give a particularly clean product.

The content of said German patent application is an important and integral part of the present invention and is included in the present patent application by reference.

The process described in this patent application can have further variants. Thus it is possible, for example, to react the TMP formate produced with a suitable amine, preferably a dialkylamine, to give TMP and dialkylformamide. Such a process is described in the German patent application entitled "Process for converting trimethylolalkane formate produced in the preparation of trimethylolalkane", reference no. 199 63 444.0 (Applicant: BASF AG).

A further possibility is to increase the yield by decomposing the high-boiling components through the addition of acid to give TMP and other products. Such a process is described in the German patent application entitled "Process for decomposing by-products formed in the synthesis of polyhydric alcohols", reference no. 199 63 437.8 (Applicant: BASF AG).

Good results have been obtainable with a TMP, purified by distillation in this or another way, which has color indices of 10 to 500 APHA, preferably 20 to 120 APHA.

The hydrogenation according to the present invention makes it possible to prepare polyhydric alcohols with APHA color indices of <10, especially TMP with color indices of ≦6 APHA.

The hydrogenation according to the invention is carried out at temperatures of 20 to 300° C., preferably 100 to 180° C., the applied pressures being 1 to 350 bar, preferably 1 to 100 bar. The residence times used in this process are 5 minutes to 4 hours, preferably 10 minutes to 1 hour. It is possible to choose a batch procedure, which is preferably carried out in a stirred tank. Another equally good possibility is to carry out the hydrogenation continuously, preferably in tubular reactors by the liquid phase or trickle method.

The catalysts used in the process according to the invention are the heterogeneous catalysts generally employed in hydrogenations. Such catalysts are known to those skilled in the art and generally contain metals of groups 3 to 12 of the periodic table, for example ruthenium, osmium, iridium, manganese, platinum, palladium, rhodium, molybdenum, tungsten, chromium, iron, cobalt, nickel, vanadium and zinc, as well as combinations of these metals, which can be used either in the form of the pure metals or in the form of compounds thereof, for example oxides or sulfides. It is preferable to use copper, nickel, ruthenium or palladium catalysts. These catalysts can be applied to the conventional supports, for example $Al_2O_3$, $SiO_2$, $TiO_2$ or carbon fibers. The resulting supported catalysts can be presented in any of the known forms, examples being rods or tablets.

It is preferable to use film catalysts of the above-mentioned metals in which the active component has been applied to a suitable fabric. Suitable fabric materials are organic or inorganic materials, or metals, which have been used for example in the form of knitted or woven fabrics. examples of suitable materials can be found in EP-A-627 944 and EP-A-564 830. examples of preferred metals are stainless steel or Kanthal. The active component can be applied by the conventional methods known to those skilled in the art, for example by vapor deposition or by the impregnation method.

One preferred embodiment of the present invention uses Raney nickel film catalysts which are obtained by the alternating vapor deposition of aluminum and nickel under reduced pressure onto suitable supports, preferably stainless steel supports, and which have catalyst film thicknesses of up to approx. 100 $\mu m$. An alternative possibility is to vapor-deposit a prefabricated Raney nickel alloy. Such catalysts are described in the patent application entitled "Film catalysts based on Raney alloys and processes for their preparation", reference no. 199 63 443.2 (Applicant: BASF AG).

Another preferred embodiment of the present invention uses palladium film catalysts which have been prepared by impregnation, preferably by the method described in EP-A-827 944.

Film catalysts have the advantage of exhibiting no abrasion under high mechanical stress and of having a good regenerability when their activity starts to decline.

The hydrogenation according to the invention using the heterogeneous catalysts described above is preferably carried out in a fixed bed and it has proved advantageous to perform the reaction in a primary reactor in a single pass. Equally good results have been obtained by carrying out the hydrogenation in a primary reactor with a secondary reactor downstream, the primary reactor operating as a loop reactor and the secondary reactor operating as a single-pass reactor. The liquid phase or trickle method can be chosen in each case.

It is also possible to use homogeneous hydrogenation catalysts, in which case the dissolved catalyst is removed after the reaction in the conventional manner, for example in a downstream evaporator.

The hydrogenation according to the invention of TMP purified beforehand by distillation can be carried out with or without the addition of another solvent. If such a solvent is used, it is added in concentrations such that the solutions employed in the hydrogenation have a TMP content of 5 to 95% by weight. The solvents used here are preferably low-boiling organic solvents such as alcohols, ethers, hydrocarbons or esters. Preferred solvents include methanol, ethanol, n-propanol, i-propanol, butanol, diethyl ether, methyl tert-butyl ether, dioxane, tetrahydrofuran and ethyl acetate. Particularly preferred solvents are methanol and tetrahydrofuran. If the hydrogenation according to the invention is carried out in the presence of an additional solvent, a separating unit is included downstream of the hydrogenation unit in order to separate the solvent from the TMP obtained in this way. examples of conventional separating units are distillation columns, film evaporators and, preferably, falling film evaporators.

The process according to the invention will now be illustrated with the aid of the following examples. The TMP used in all the examples had been prepared as follows:

An apparatus consisting of two heatable stirred tanks with an overall capacity of 72 l, interconnected by overflow tubes, was charged continuously with fresh aqueous formaldehyde solution (4300 g/h) in the form of a 40% aqueous solution, and n-butyraldehyde (1800 g/h), and with fresh trimethylamine as catalyst (130 g/h) in the form of a 45% aqueous solution. The reactors were heated to a constant temperature of 40° C.

The discharge was passed directly into the top of a falling film evaporator with attached column (superheated steam at 11 bar), where it was separated by distillation under atmospheric pressure into a low-boiling top product, essentially containing n-butyraldehyde, ethylacrolein, formaldehyde, water and trimethylamine, and a high-boiling bottom product.

The top product was continuously condensed and recycled into the reactors described above.

The high-boiling bottom product from the evaporator (approx. 33.5 kg/h) was treated continuously with fresh trimethylamine catalyst (50 g/h) in the form of a 45% aqueous solution, and transferred to a heatable, packed tubular reactor with an empty volume of 12 l. The reactor was heated to a constant temperature of 40° C.

The discharge from the secondary reactor was passed continuously into the top of another distillation device for separation of the formaldehyde (superheated steam at 11 bar), where it was separated by distillation into a low-boiling top product, essentially containing ethylacrolein, formaldehyde, water and trimethylamine, and a high-boiling bottom product. The low-boiling top product (27 kg/h) was continuously condensed and recycled into the first stirred tank, while the high-boiling bottom product was collected.

In addition to water, the resulting bottom product contained essentially dimethylolbutyraldehyde, form-aldehyde and traces of monomethylolbutyraldehyde. This bottom product was then subjected to continuous hydrogenation. This was done by hydrogenating the reaction solution at 90 bar and 115° C. in a primary reactor by the loop/trickle method and in a downstream secondary reactor by the loop method. The catalyst was prepared analogously to D of DE 198 09 418. It contained 24% of CuO, 20% of Cu and 46% of $TiO_2$. The apparatus used consisted of a heated primary reactor with a length of 10 m (internal diameter: 27 mm) and a heated secondary reactor with a length of 5.3 m (internal diameter: 25 mm). The loop throughput was 25 l/h of liquid and the reactor feed was adjusted to 4 kg/h, corresponding to a hydrogenation discharge of 4 kg/h.

After hydrogenation, the TMP was withdrawn from the bottom of the column and worked up by distillation according to the method described in examples 2 and 3 of the German patent application entitled "Process for the purification, by continuous distillation, of trimethylolpropane prepared by hydrogenation", reference no. 199 63 435.1 (Applicant: BASF AG). The TMP used in some of the examples was taken from the first distillative purification column (grade A). The TMP used in other examples originated from the second distillative purification (grade B).

The TMP already hydrogenated by the process according to the invention can be subjected to a further hydrogenation in order to improve the color index, preferably using a different catalyst.

The indicated APHA color indices were measured with a LICO 200 instrument from the company Dr. Lange. For better reproducibility, the TMP samples were measured as a 50% mixture with methanol rather than in the pure form. The standard procedure was to perform 2 measurements in each case. The value obtained was then multiplied by a factor of 2 to convert to a 100% TMP solution. As this method only allows color indices to be determined down to a lower limit of 6 APHA, the indication ≦6 APHA is given below in cases where such a value was measured.

EXAMPLE 1

A grade A TMP was hydrogenated which had a color index of 106 APHA and a TMP content of 99.1%. The hydrogenation was carried out in a tubular reactor by the liquid phase method on 130 ml of a catalyst consisting of 0.5% Pd-on-$Al_2O_3$. The temperature was 120° C., the pressure was 20 bar and the feed was adjusted to 0.85 ml/min. The TMP obtained after hydrogenation had an APHA color index of 48.

EXAMPLE 2

A grade A TMP was hydrogenated in a tubular reactor by the liquid phase method on 130 ml of a catalyst consisting of 60% CuO-on-$TiO_2$ (prepared according to DE-A-198 09 418), at a temperature of 100° C. and a pressure of 30 bar. The feed was adjusted to 1.00 ml/min. The TMP obtained after hydrogenation had an APHA color index of 34.

EXAMPLE 3

The procedure was as described in example 2, the temperature being adjusted to 120° C. The TMP obtained after hydrogenation had an APHA color index of 24.

EXAMPLE 4

A grade A TMP was used which had a color index of 106 APHA and a TMP content of 99.1%. The TMP was hydrogenated in the form of a 50% methanolic solution by the liquid phase method on 130 ml of a Cu/$TiO_2$ catalyst containing 60% of CuO, at a pressure of 30 bar and a temperature of 140° C. and with a feed of 1.0 ml/min. The product obtained after hydrogenation was freed of methanol on a rotary evaporator to give a TMP with an APHA color index of ≦6.

EXAMPLE 5

The hydrogenation was carried out as described in example 4, the feed being adjusted to 2.0 ml/min. The product obtained after hydrogenation had an APHA color index of 10.

EXAMPLE 6

A grade A TMP with a color index of 84 APHA and a TMP content of 99.1% was hydrogenated as described in example 5. The hydrogenation discharge obtained was freed of methanol in a falling film evaporator at 120° C. and a pressure of 20 mbar. According to gas chromatographic analysis, the Sambay discharge contained 99.1% of TMP and less than 0.1% of methanol. The partially condensed top product contained 1.5% of TMP. The TMP obtained had an APHA color index of 18.

EXAMPLE 7

A grade A TMP with a color index of 64 APHA and a TMP content of 99.1% was hydrogenated as described in example 5. The hydrogenation discharge obtained was freed of methanol in a falling film evaporator at 130° C. and under atmospheric pressure with 10 Nl/h of $N_2$ as the stripping gas. According to gas chromatographic analysis, the Sambay discharge contained 99.1% of TMP and was free of methanol. 0.7% of TMP was found in the top product. The TMP prepared had a color index of 20 APHA.

EXAMPLES 8 TO 11

A grade A or B TMP with a purity of 99.1% was used. The hydrogenation was carried out in a 1.5 l stirred apparatus with a gas dispersion stirrer operating at 1400 $min^{-1}$. The film catalysts used are specified in the table below; they had been prepared according to EP-A-827 944 and were incorporated in monolithic form. They were prepared by impregnation onto metal fabrics consisting of the material 1.4767, which were then crimped to form a packing of the conventional dimensions. 1300 g of molten TMP were introduced and electronically heated to the appropriate temperature before 40 Nl/h of hydrogen were passed through the liquid TMP under atmospheric pressure. The results are shown in the table below.

| Ex. | Catalyst | mg metal/$m^2$ | Pitch [mm] | RT [min] | Temp. [° C.] | CI (educt) [APHA] | CI (product) [APHA] | Grade of TMP used |
|---|---|---|---|---|---|---|---|---|
| 8 | Pd 1.4767 | 504 | 1.0 | 15 | 120 | 56 | ≦6 | B |
| 9 | Pd/Ni 1.4767 | 634 Pd 89 Ni | 1.0 | 15 | 120 | 56 | 12 | B |
| 10 | Pd 1.4767 | 494 | 1.0 | 15 | 120 | 78 | 18 | A |
| 11 | Pd 1.4767 | 286 | 1.0 | 15 | 120 | 78 | 20 | A |

RT = residence time
CI = color index

EXAMPLES 12 TO 18

The TMP used as the starting material was grade B and had a purity of 99.1%.

The appropriate film catalyst (monolithic form) was introduced into a 300 ml stirred autoclave with gas dispersion stirrer (1400 rpm). The Pd and Ru film catalysts were prepared according to EP 0 827 944 by impregnation onto metal fabric, which was then rolled up to form a monolithic packing (pitch: 1.5 mm). After 245 g of molten TMP had been introduced and electronically heated to the appropriate temperature, the appropriate hydrogen pressure was applied. Samples were taken at given intervals for determination of the color index.

| Ex. | Catalyst | mg metal/m² | RT [min] | Temp. [° C.] | Pressure [bar] | CI (educt) [APHA] | CI (product) [APHA] |
|---|---|---|---|---|---|---|---|
| 12 | Ru | 578 | 60 | 140 | 30 | 42 | 16 |
| 13 | Ru | 578 | 60 | 140 | 1 | 42 | 34 |
| 14 | Pd + Ru* | 578 | 60 | 140 | 30 | 40 | 14 |
| 15 | Raney Ni** | 500 | 60 | 140 | 30 | 32 | 14 |
| 16 | Raney | 3630 | 60 | 140 | 10 | 38 | 6 |
| 17 | Raney Ni** | 3630 | 60 | 140 | 1 | 38 | 20 |
| 18 | Raney Ni** | 3630 | 15 | 140 | 20 | 38 | 8 |

*Both the Ru and Pd film catalysts were used together as a mixture in the hydrogenation.
**The Raney nickel catalysts were obtained according to example 1 of the German patent application entitled "Film catalysts based on Raney alloys and process for their preparation", reference no. 199 63 443.2 (Applicant: BASF AG).

EXAMPLES 19 TO 21

The experiments were performed analogously to example 18 except that Pd-on-1.4767 fabric (504 mg metal/m², pitch 1.5 mm) was used as the film catalyst. Different TMP grades were hydrogenated under the conditions of example 12:

| Ex. | Starting material | TMP content | CI (educt) | CI (product) |
|---|---|---|---|---|
| 19 | TMP (grade B) | 99.0% | 38 | 16 |
| 20 | Dehydrated crude TMP* | 83% | >600 | >600 |
| 21 | Dehydrated crude TMP freed of high-boiling components** | 94% | >600 | >600 |

*dehydrated according to the German patent application entitled "Improving the color index of polyhydric alcohols by continuous distillation", reference no. 199 63 435.1 (Applicant: BASF AG), and taken after separation of the water and low-boiling components This example shows that only TMP grades which have been purified beforehand by distillation are suitable for improvement of the color index by hydrogenation.

EXAMPLE 22

A grade A TMP with a color index of 120 APHA was hydrogenated under the conditions of example 16, said hydrogenation being carried out at 30 bar (instead of 10 bar). The TMP obtained after hydrogenation had a color index of 18 APHA.

EXAMPLES 23 TO 24

The grade B TMP used as the starting material had a color index of 56 APHA and a purity of 99.1%. The hydrogenation was carried out in a tubular reactor packed with 8 inserts of rolled-up Pd/Kanthal film catalyst. The TMP solution was passed over the catalyst bed by the liquid phase or trickle method and part of the TMP reaction discharge was recycled into the reactor (loop method). The amount of hydrogen was 20–40 l/h.

After the stationary state had been reached, samples were withdrawn for determination of the color index.

| Ex. | Liquid phase/ trickle | Amount recycled [l/h] | Amount of H₂ [l/h] | Feed [ml/min] | RT [min] | Temp. [° C.] | CI (product) [APHA] |
|---|---|---|---|---|---|---|---|
| 23 | LP | 20 | 20 | 2.0 | 60 | 120 | 18 |
| 24 | T | 12 | 20 | 2.0 | 60 | 120 | 18 |

EXAMPLE 25

The experiment was carried out analogously to example 24 except that a grade B TMP with a color index of 16 APHA was used as the educt, the amount recycled was 20 l/h and the amount of H₂ was 60 l/h. Hydrogenation reduced the color index to ≦6 APHA.

We claim:

1. A process for improving the color index of polyhydric alcohols, selected from the group consisting of trimethylolethane, trimethylolpropane, trimethylolbutane, neopentyl glycol and pentaerythritol, by catalytic hydrogenation, wherein the polyhydric alcohol used in the hydrogenation has been purified by distillation following is preparation.

2. A processes claimed in claim 1 wherein the polyhydric alcohol originates from a inorganic or organic Cannizzaro process or from a hydrogenation process.

3. A process as claimed in claim 1 wherein the polyhydric alcohol used in the hydrogenation has a product content of >95%.

4. A process as claimed in claim 1 wherein heterogeneous catalysts of metals of groups 3 to 12 of the periodic table, either in the form of the pure metals or in the form of compounds thereof, are used in the hydrogenation.

5. A process as claimed in claim 4 wherein catalysts applied to supports, in the form of rods or tablets, or film catalysts on organic or inorganic fabric materials or on metals, are used.

6. A process as claimed in claim 5 wherein film catalysts containing Pd, Ru or Raney nickel are used in any of the possible forms of the fabric.

7. A process as claimed in claim 1 wherein the hydrogenation is carried out at temperatures of 20 to 300° C., and pressures of 1 to 350 bar.

8. A process as claimed in claim 1 wherein the polyhydric alcohol used in the catalytic hydrogenation has a residence time of is from 5 minutes to 4 hours.

9. A process as claimed in claim 1 wherein the hydrogenation is carried out batchwise, or in a stirred tank, or continuously, preferably in tubular reactors by the liquid phase or trickle method.

10. A process as claimed in claim 1 wherein the polyhydric alcohol is trimethylolpropane.

11. A process as claimed in claim 2 wherein the polyhydric alcohol originates from a hydrogenation process.

12. A process as claimed in claim 3 wherein trimethylolpropane has a product content of >98%.

13. A process as claimed in claim 4 wherein the metals are selected from Cu, Raney Nickel, Pd or Ru, or combinations thereof.

14. A process as claimed in claim 5 wherein the supports are selected from $Al_2O_3$ or $TiO_2$, in any form.

15. A process as claimed in claim 7 wherein the hydrogenation is carried out at temperatures of 100 to 180° C.

16. A process as claimed in claim 15 wherein the hydrogenation is carried out at pressures of 1 to 100 bar.

17. A process as claimed in claim 16 wherein the hydrogenation is carried out at pressures of 1 to 50 bar.

18. A process as claimed in claim 8 wherein the residence time is from 10 minutes to 60 minutes.

* * * * *

UNITED STATES PATENT AND TRADEMARK OFFICE
CERTIFICATE OF CORRECTION

PATENT NO. : 6,586,642 B2  
DATED : July 1, 2003  
INVENTOR(S) : Dernbach et al.

It is certified that error appears in the above-identified patent and that said Letters Patent is hereby corrected as shown below:

Column 10,
Line 47, "preferably" should be -- or --.

Signed and Sealed this

Seventh Day of October, 2003

JAMES E. ROGAN
*Director of the United States Patent and Trademark Office*